United States Patent
Yu et al.

(10) Patent No.: US 7,064,228 B1
(45) Date of Patent: Jun. 20, 2006

(54) SPIRO SILANE COMPOUND AND ORGANIC ELECTROLUMINESCENT DEVICE USING THE SAME

(75) Inventors: Chen-Ping Yu, Longtan (TW); Pei-Chi Wu, Kaohsiung (TW)

(73) Assignee: AU Optronics Corp., Hsinchu (TW)

( * ) Notice: Subject to any disclaimer, the term of this patent is extended or adjusted under 35 U.S.C. 154(b) by 0 days.

(21) Appl. No.: 11/274,700

(22) Filed: Nov. 15, 2005

(30) Foreign Application Priority Data

Sep. 21, 2005 (TW) ................ 94132723 A

(51) Int. Cl.
*C07F 7/08* (2006.01)
(52) U.S. Cl. .............. 556/489; 313/506; 313/504; 428/690; 428/917
(58) Field of Classification Search ........... 556/489; 313/504, 506; 428/690, 917
See application file for complete search history.

(56) References Cited

U.S. PATENT DOCUMENTS 6,310,231 B1  10/2001  Igarashi et al. ........... 556/489

2005/0064238 A1  3/2005  Lee et al. ............... 428/690

FOREIGN PATENT DOCUMENTS

WO    WO2004058911    7/2004

*Primary Examiner*—Samuel Barts
(74) *Attorney, Agent, or Firm*—Thomas, Kayden, Horstemeyer & Risley

(57) ABSTRACT

A spiro silane compound can be applied in the organic electroluminescent device as the host material of the light emission layer, and represented by the following formula:

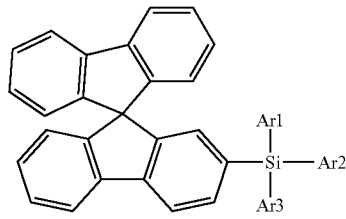

wherein $Ar_1$, $Ar_2$ and $Ar_3$ are independently selected from the group consisting of a phenyl group, a spirobifluorene group and an alkyl group.

17 Claims, 1 Drawing Sheet

SPIRO SILANE COMPOUND AND ORGANIC ELECTROLUMINESCENT DEVICE USING THE SAME

This application claims the benefit of Taiwan application Serial No. 094132723, filed Sep. 21, 2005, the subject matter of which is incorporated herein by reference.

BACKGROUND OF THE INVENTION

1. Field of the Invention

The invention relates in general to a spiro silane compound and an organic electroluminescent device using the same, and more particularly to the spiro silane compound applied in the organic electroluminescent device as the host material of the light emitting layer for effectively increasing the light efficiency.

2. Description of the Related Art

Use of an organic electroluminescence device (OELD) in the flat panel displays possesses several competitive advantages, such as self illumination, high brightness, wide viewing angle, vivid contrast, quick response, broad range of operating temperature, high luminous efficiency and uncomplicated process of fabrication. Thus, the OELD represents a promising technology for display applications and receives the worldwide attention in recent years.

The typical structure of OELD is mainly constructed by interposing an organic light emitting layer between an anode and a cathode. A hole injection layer (HIL) and a hole transport layer (HTL) are interposed between the anode and the organic light emitting layer. An electron transport layer (ETL) is interposed between the cathode and the organic light emitting layer. Also, an electron injection layer (EIL) can be disposed between the electron transport layer and the cathode, for improving the performance of OELD. This OELD structure facilitates the electron flow from the cathode to the anode.

Nowadays, the most common materials of the organic light emitting layer can be divided into two groups including a group of silane compounds represented by the formula (I) and a group of spiro compound represented by the following formula (II). In the formula (I), R represents an alkyl group, a heteroaryl group or an alkynyl group, and each of $Ar_1$, $Ar_2$ and $Ar_3$ represents a heteroaryl group. However, many manufacturers and consumers are still looking forward to the advance of the device efficiency.

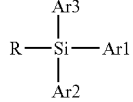
(I)

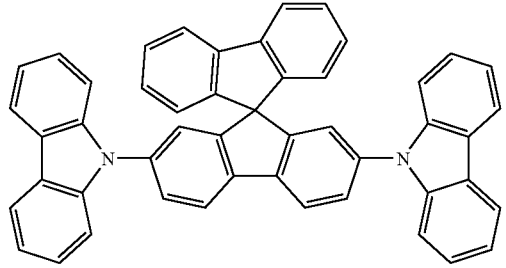
(II)

SUMMARY OF THE INVENTION

It is therefore an object of the invention to provide a spiro silane compound and an organic electroluminescent device using the same, for effectively increasing the light efficiency of the device.

The invention achieves the objects by providing a Spiro silane compound of formula (III):

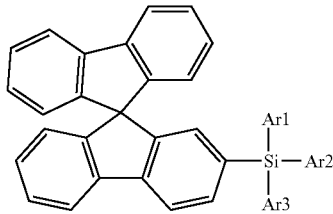
(III)

wherein $Ar_1$, $Ar_2$ and $Ar_3$ are independently selected from the group consisting of a phenyl group, a spirobifluorene group and an alkyl group.

The invention achieves the objects by providing an organic electroluminescence device (OELD), at least comprising an anode, a hole transport layer formed above the anode, an organic light emitting layer formed above the hole transport layer, an electron transport layer formed above the organic light emitting layer, and a cathode formed above the electron transport layer. The organic light emitting layer includes a spiro silane compound of formula (III) as the host.

Other objects, features, and advantages of the invention will become apparent from the following detailed description of the preferred but non-limiting embodiments. The following description is made with reference to the accompanying drawings.

DETAILED DESCRIPTION OF THE INVENTION

Figure 1:
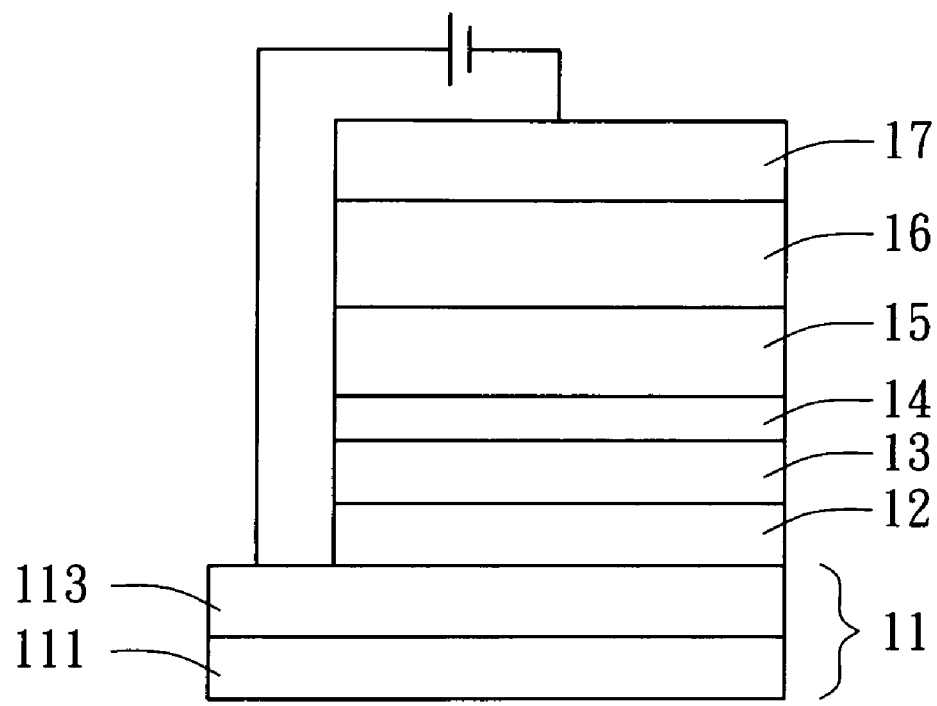
FIG. 1 schematically illustrates an organic electroluminescence device (OELD) according to the device example of the invention.

In the present invention, a spiro silane compound is provided and applied in the organic electroluminescent device as the host material of the light emitting layer for effectively increasing the device efficiency.

The spiro silane compound of the present invention is represented by the formula (III):

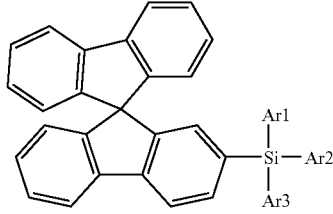
(III)

wherein $Ar_1$, $Ar_2$ and $Ar_3$ are independently selected from the group consisting of a phenyl group, a spirobifluorene group and an alkyl group.

When each of $Ar_1$, $Ar_2$ and $Ar_3$ represents a phenyl group, the spiro silane compound is 2-triphenylsily-9,9'-spirobifluorene, and represented by the formula (III-1):

(III-1)

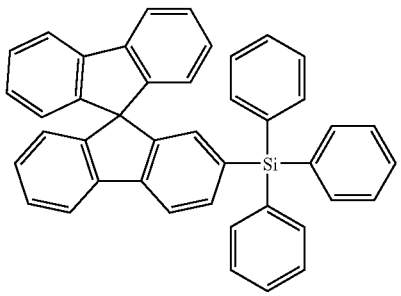

When each of $Ar_1$, and $Ar_2$ represents a phenyl group, and $Ar_3$ represents a spirobifluorene group, the spiro silane compound is diphenyl-di(2-9,9'-spirobifluorenyl) silane, and represented by the formula (III-2):

(III-2)

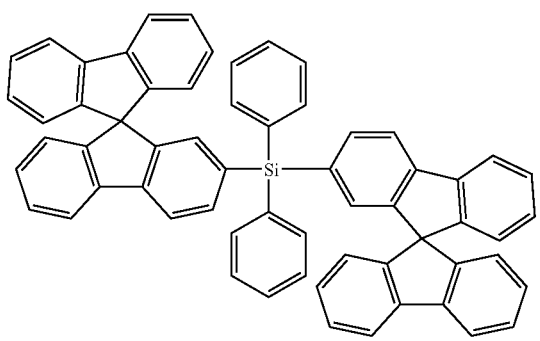

When each of $Ar_1$, and $Ar_2$ represents a spirobifluorene group, and $Ar_3$ represents a phenyl group, the spiro silane compound is phenyl-tri(2-9,9'-spirobifluorenyl) silane, and represented by the formula (III-3):

(III-3)

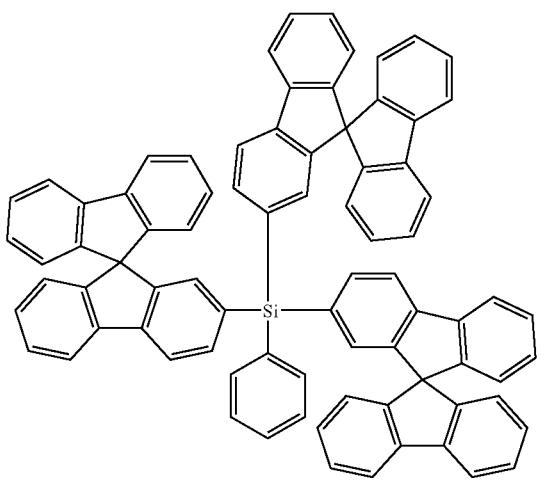

When each of $Ar_1$, $Ar_2$ and $Ar_3$ represents a spirobifluorene group, the spiro silane compound is tetra(2-9,9'-spirobifluorenyl) silane, and represented by the formula (III-4):

(III-4)

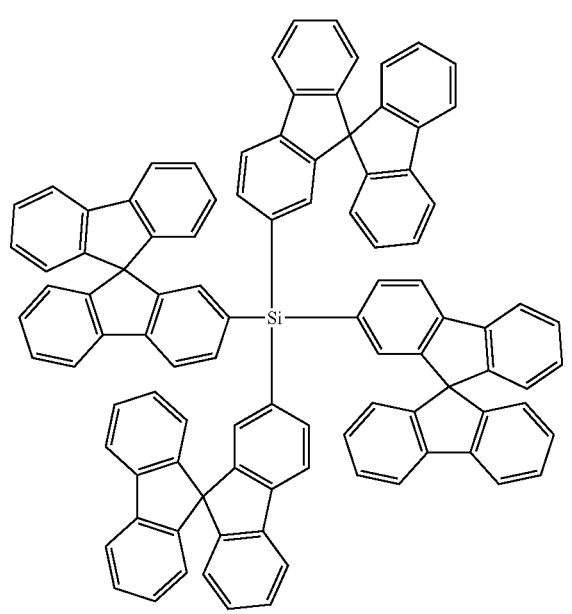

SYNTHESIS EXAMPLES

Synthesis of Compound (III-1)

The synthesis of 2-triphenylsily-9,9'-spirobifluorene (III-1) can be represented by the reaction of scheme 1, and further explained in detail in the following description.

In a nitrogen atmosphere, 10 g (25.3 mmol) of 2-bromo-9,9'-spirobifluorene and 300 ml of tetrahydrofuran (THF) were added to a round-bottom flask. Next, 10.1 ml (25.3 mmol, 2.5 M) of n-butyl lithium was added dropwise slowly into the round-bottom flask at a temperature of −78° C. After mixed and reacted for 30 min, 8.2 g (27.8 mmol) triphenylsilyl chloride with 50 ml THF were added dropwise slowly into the round-bottom flask at a temperature of −78° C. After reacted at room temperature for 24 hours, the resulting mixture was subjected to extraction with a mixed solvent (ethyl acetate: $H_2O$), dried over anhydrous $MgSO_4$, filtered, and condensed. Then, the crude product was purified by sublimation twice, and 8.7 g of pure 2-triphenylsily-9,9'-spirobifluorene was collected.

Scheme 1

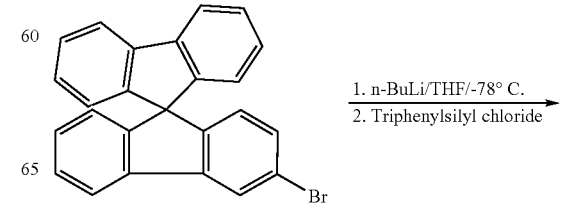

-continued

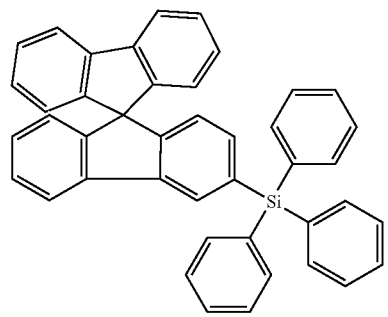

Synthesis of Compound (III-2)

The synthesis of diphenyl-di(2-9,9'-spirobifluorenyl) silane (III-2) can be represented by the reaction of scheme 2. The procedure in detail is described below.

In a nitrogen atmosphere, 10 g (25.3 mmol) of 2-bromo-9,9'-spirobifluorene and 300 ml of tetrahydrofuran (THF) were added to a round-bottom flask. Next, 10.1 ml (25.3 mmol, 2.5 M) of n-butyl lithium was added dropwise slowly into the round-bottom flask at a temperature of −78° C. After mixed and reacted for 30 min, 3.5 g (13.9 mmol) dichlorodiphenyl silane were added dropwise slowly into the round-bottom flask at −78° C. After reacted at room temperature for 24 hours, the resulting mixture was subjected to extraction with a mixed solvent (ethyl acetate: $H_2O$), dried over anhydrous $MgSO_4$, filtered, and condensed. Then, the crude product was purified by sublimation twice, and 1.0 g of pure diphenyl-di(2-9,9'-spirobifluorenyl) silane was collected.

Scheme 2

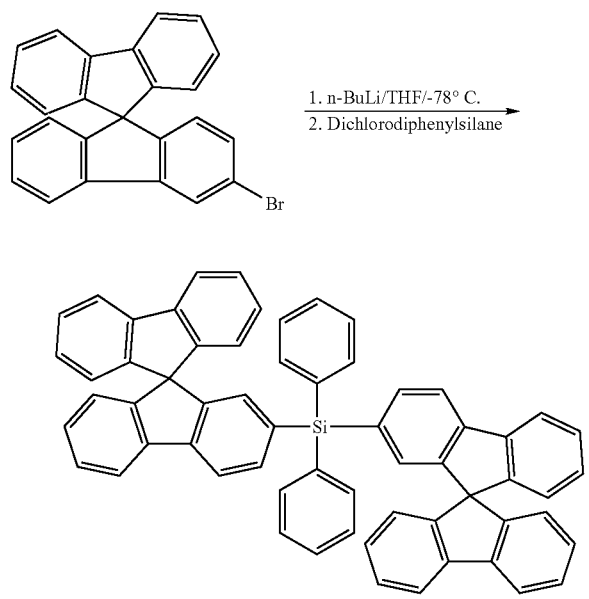

The spiro silane compound (III) of the present invention applied in the organic electroluminescent device as the host material of the light emitting layer does effectively increase the device efficiency. In the following device example, five organic electroluminescent devices are constructed and examined by a series of tests. The test results are summarized in table 1.

DEVICE EXAMPLE

FIG. 1 schematically illustrates an organic electroluminescence device (OELD) according to the device example of the invention. As shown in FIG. 1, the OELD mainly comprises an anode 11, a light emitting layer 15 and a cathode 17. To make the anode 11, for example, a glass substrate 111 with indium tin oxide (ITO) film 113 was provided and then washed by cleaning agent, acetone, and ethanol with ultrasonic agitation. After drying with nitrogen flow, the ITO film 113 was subjected to uv/ozone treatment. The layers laminated on the ITO 113 can be formed at a film formation pressure of $10^{-4}$ Pa. The cathode 17 could be a multi-metallic layer including lithium fluoride (LiF) and aluminum (Al). Also, a hole injection layer (HIL) 12, a hole transport layer (HTL) 13 and a buffer layer 14 are formed between the anode 11 and the light emitting layer 15. An electron transport layer (ETL) 16 is formed between the cathode 17 and the light emitting layer 15. It is, of course, understood that an electron injection layer (EIL) (not shown in FIG. 1) is not necessary to the OELD, but can be existed for increasing injection ability of the electrons and holes.

In this device example, the hole injection layer (HIL) 12 of each OELD is in a thickness of 60 nm, and contains 4,4',4''-tri(N-(2-naphthyl)-N-aniline)-triphenyl amine (2T-NATA).

(2T-NATA)

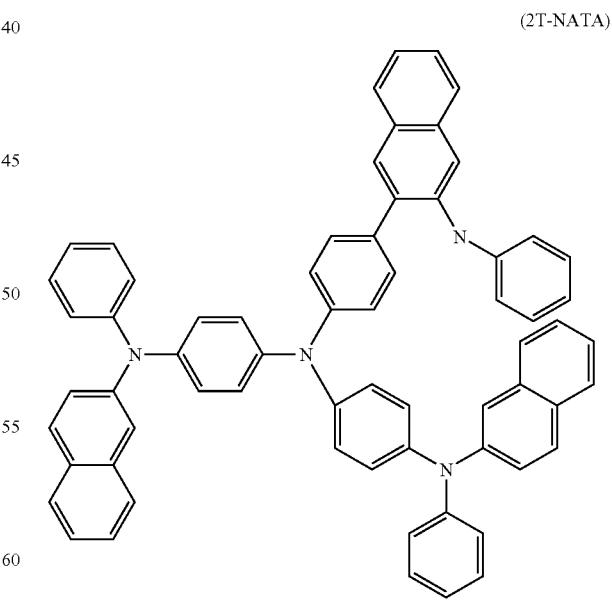

In this device example, the hole transport layer (HTL) 13 of each OELD is in a thickness of 20 nm, and contains N,N'-di-1-naphthyl-N,N'-diphenyl-1,1'-biphenyl-1,1'-biphenyl-4,4'-diamine (NPB).

(NPB)

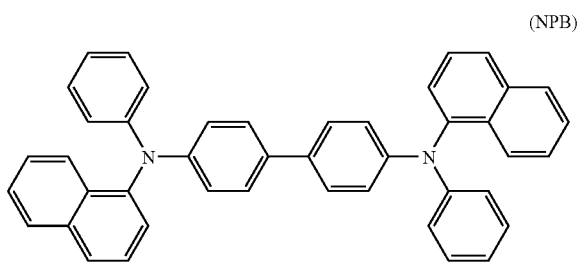

In this device example, the buffer layer 14 of each OELD is in a thickness of 10 nm, and contains N,N'-dicarbazole-1,3-benzene (mCP).

(mCP)

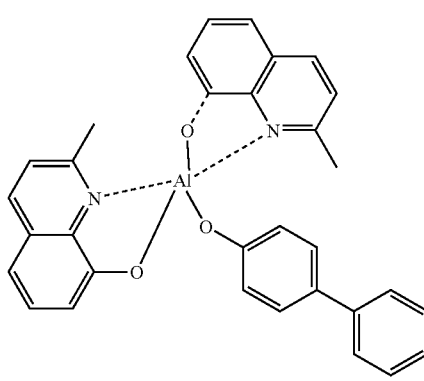

In this device example, the electron transport layer (ETL) 16 of each OELD contains [(1,1'-Bisphenyl-4-olato)bis(2-methyl-8-quinolinplate —N1,08)Aluminum (III)] (BAlq).

(BAlq)

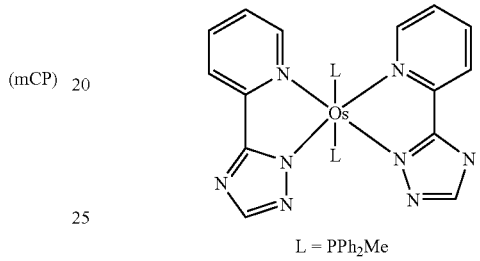

The cathode 17 includes a lithium fluoride (LiF) layer in a thickness of 10 Å, and an aluminum (Al) layer in a thickness of 100 nm.

The light emitting layer 15 is in a thickness of 30 nm. Also, the phosphorescent light emitting materials are selected from an Ir complex, a Pt complex or an Os complex. An example of the Ir complex is compound Ir-1, which is selected as the dopant of the light emitting layer 15, and the doping ratio is 18%.

(Pt complex)

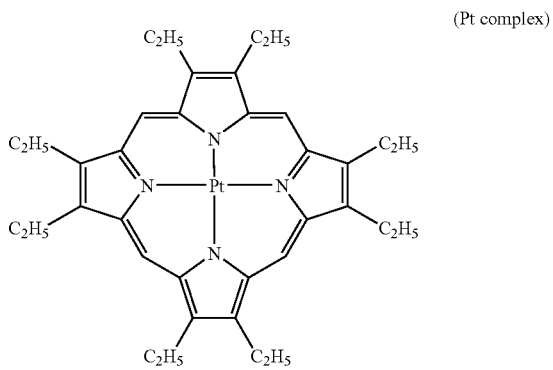

(Os complex)

L = PPh$_2$Me (Ir-1)

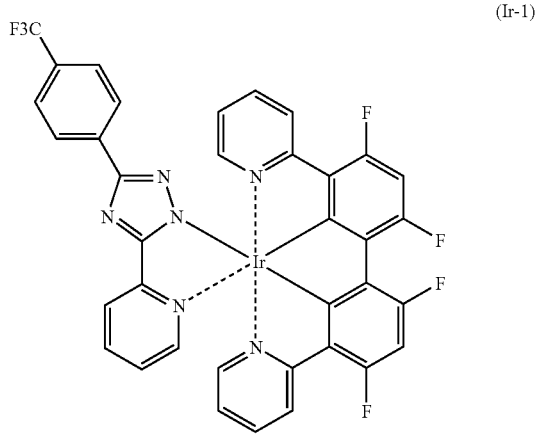

In the device 1, 2-triphenylsily-9,9'-spirobifluorene (formula III-1) is selected as the host material of the light emitting layer 15, and the electron transport layer 16 (BAlq) is in a thickness of 45 nm.

In the device 2, 2-triphenylsily-9,9'-spirobifluorene (formula III-1) is also selected as the host material of the light emitting layer 15, but the electron transport layer 16 (BAlq) is in a thickness of 30 nm.

In the device 3, diphenyl-di(2-9,9'-spirobifluorenyl)silane (formula III-2) is selected as the host material of the light emitting layer 15, and the electron transport layer 16 (BAlq) is in a thickness of 30 nm.

In the comparative device 1, N,N'-dicarbazole-1,3-benzene (mCP) is selected as the host material of the light emitting layer 15, and the electron transport layer 16 (BAlq) is in a thickness of 45 nm.

In the comparative device 2, N,N'-dicarbazole-1,3-benzene (mCP) is also selected as the host material of the light emitting layer 15, but the electron transport layer 16 (BAlq) is in a thickness of 30 nm.

Accordingly, five organic electroluminescent devices can be simply represented as below:

Device 1 ITO (750 nm)/2T-NATA (60 nm)/NPB (20 nm)/mCP (10 nm)/(III-1): Ir-1 (100:18) (30 nm)/BAlq (45 nm)/LiF (10 Å)/Al (100 nm)

Device 2 ITO (750 nm)/2T-NATA (60 nm)/NPB (20 nm)/mCP (10 nm)/(III-1): Ir-1(100:18) (30 nm)/BAlq (30 nm)/LiF (10 Å)/Al (100 nm)

Device 3 ITO (750 nm)/2T-NATA (60 nm)/NPB (20 nm)/mCP (10 nm)/(III-2): Ir-1 (100:18) (30 nm)/BAlq (30 nm)/LiF (10 Å)/Al (100 nm)

comparative ITO (750 nm)/2T-NATA (60 nm)/NPB (20 nm)/mCP (10 nm)/device 1 mCP: Ir-1 (100:18) (30 nm)/BAlq (45 nm)/LiF (10 Å)/Al (100 nm)

comparative ITO (750 nm)/2T-NATA (60 nm)/NPB (20 nm)/mCP (10 nm)/device 2 mCP: Ir-1 (100:18) (30 nm)/BAlq (30 nm)/LiF (10 Å)/Al (100 nm)

A series of measurements are conducted, and the results of devices properties are shown in table 1.

TABLE 1

| Example | Operation Voltage (V) | Brightness (cd/m$^2$) | CIE chromaticity coordinates (X axis) | CIE chromaticity coordinates (Y axis) | Efficiency (cd/A) |
| --- | --- | --- | --- | --- | --- |
| device 1 | 11.2 | 1000 | 0.17 | 0.32 | 11.1 |
| device 2 | 10.5 | 1000 | 0.17 | 0.29 | 7.7 |
| device 3 | 10.7 | 1000 | 0.17 | 0.29 | 7.2 |
| Comparative device 1 | 11.5 | 1000 | 0.17 | 0.28 | 6.7 |
| Comparative device 2 | 10.6 | 1000 | 0.17 | 0.28 | 5.8 |

The results has indicated that CIE x is identical, the operation voltage and CIE y are almost the same when each device generates light of 1000 nits (cd/m$^2$). However, the light efficiency of the device using the spiro silane compound of the present invention is effectively improved. For example, the light efficiency of the comparative device 1 (using compound mCP known in the art as the host of light emitting layer) is only 6.7 cd/A, but the light efficiency of the device 1 (using compound III-1 of the invention as the host of light emitting layer) is increased to 11.1 cd/A. Also, the light efficiencies of the devices 2 (using compound III-1 as the host of light emitting layer) and 3 (using compound III-2 as the host of light emitting layer) are higher than that of the comparative device 2 (using compound mCP as the host of light emitting layer).

While the invention has been described by way of example and in terms of the preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A spiro silane compound represented by a general formula:

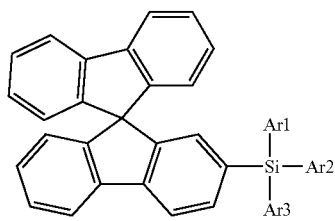

wherein Ar$_1$, Ar$_2$ and Ar$_3$ are independently selected from the group consisting of a phenyl group, a spirobifluorene group and an alkyl group.

2. The spiro silane compound of claim 1, wherein each of Ar$_1$, Ar$_2$ and Ar$_3$ represents the phenyl group, the spiro silane compound is 2-triphenylsily-9,9'-spirobifluorene, and represented by the following formula:

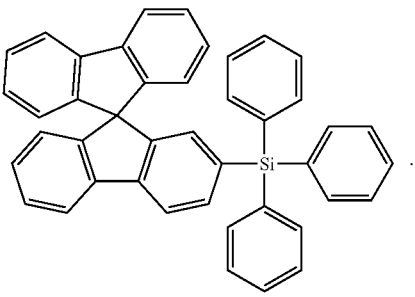

3. The spiro silane compound of claim 1, wherein each of Ar$_1$, and Ar$_2$ represents the phenyl group, and Ar$_3$ represents the spirobifluorene group, the spiro silane compound is diphenyl-di(2-9,9'-spirobifluorenyl) silane, and represented by the following formula:

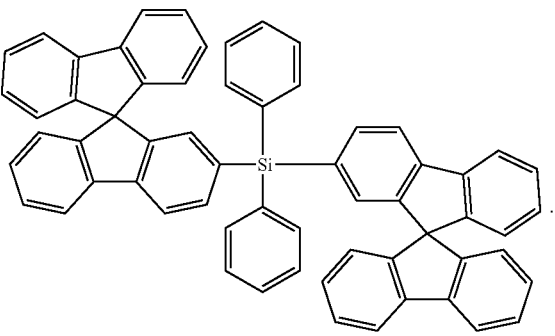

4. The spiro silane compound of claim 1, wherein each of Ar$_1$, and Ar$_2$ represents the spirobifluorene group, and Ar$_3$ represents the phenyl group, the spiro silane compound is phenyl-tri(2-9,9'-spirobifluorenyl) silane, and represented by the following formula:

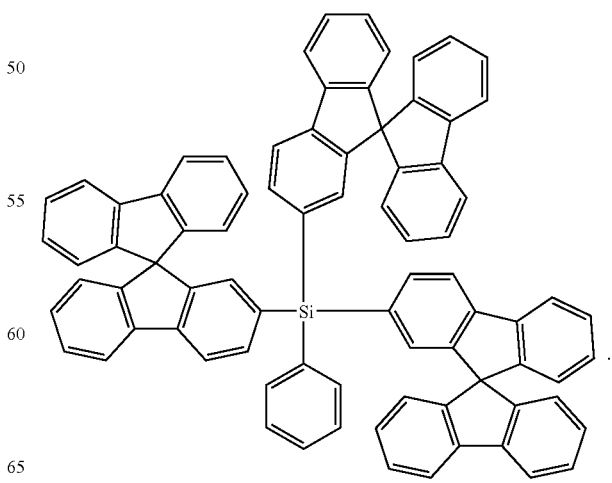

5. The spiro silane compound of claim 1, wherein each of $Ar_1$, $Ar_2$ and $Ar_3$ represents the spirobifluorene group, the spiro silane compound is tetra(2-9,9'-spirobifluorenyl) silane, and represented by the following formula:

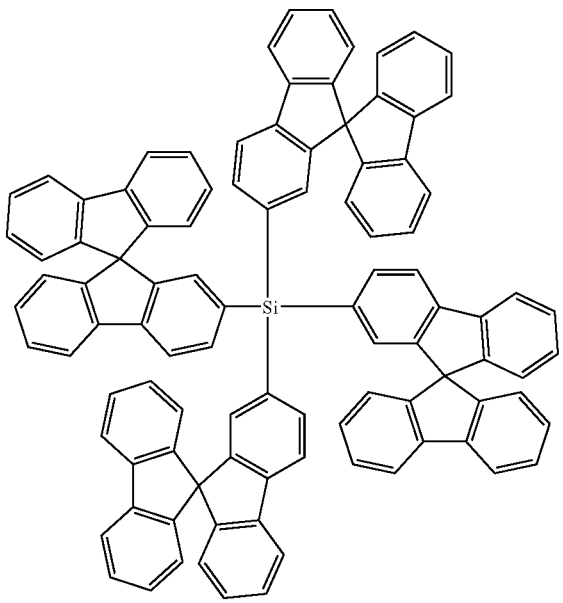

6. An organic electroluminescence device (OELD), comprising:
an anode;
a hole transport layer formed over the anode;
an organic light emitting layer formed over the hole transport layer;
an electron transport layer formed above the organic light emitting layer, the electron transport layer including a Spiro silane compound represented by the general formula:

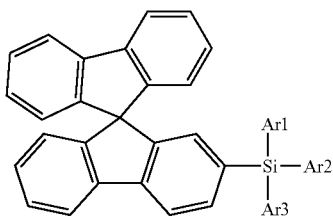

wherein $Ar_1$, $Ar_2$ and $Ar_3$ are independently selected from the group consisting of a phenyl group, a spirobifluorene group and an alkyl group; and
a cathode formed over the electron transport layer.

7. The OELD of claim 6, wherein the spiro silane compound is a host material of the organic light emitting layer.

8. The OELD of claim 6, wherein the organic light emitting layer comprises a metal complex as a dopant.

9. The OELD of claim 8, wherein the metal complex comprises an iridium complex, a Pt complex or an Os complex.

10. The OELD of claim 8, wherein the metal complex is an iridium complex, and represented by the following formula:

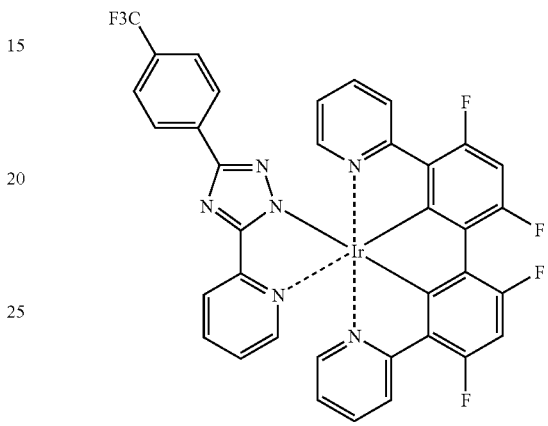

11. The OELD of claim 6, wherein the hole transport layer comprises N,N'-di-1-naphthyl-N,N'-diphenyl-1,1'-biphenyl-1,1'-biphenyl-4,4'-diamine (NPB).

12. The OELD of claim 6, further comprising:
a hole injection layer disposed between the anode and the hole transport layer.

13. The OELD of claim 12, wherein the hole injection layer comprises 4,4',4"-tri(N-(2-naphthyl)-N-aniline)-triphenyl amine (2T-NATA).

14. The OELD of claim 6, wherein the electron transport layer comprises 1,1'-Bisphenyl-4-olato)bis(2-methyl-8-quinolinplate-N1,08)Aluminum (III) (BAlq).

15. The OELD of claim 6, further comprising:
an electron injection layer disposed between the cathode and the electron transport layer.

16. The OELD of claim 6, further comprising:
a buffer layer disposed between the organic light emitting layer and the hole transport layer.

17. The OELD of claim 16, wherein the buffer layer comprises N,N'-dicarbazole-1,3-benzene (mCP).

* * * * *